United States Patent
Mitsui et al.

(10) Patent No.: US 8,365,737 B2
(45) Date of Patent: Feb. 5, 2013

(54) EQUIPMENT FOR PREVENTING AND TREATING PELVIC ORGAN PROLAPSE

(75) Inventors: Keiko Mitsui, Tokyo (JP); Makoto Shimada, Tokyo (JP)

(73) Assignee: Women's Medical Research, Inc., Tokyo (JP)

( * ) Notice: Subject to any disclaimer, the term of this patent is extended or adjusted under 35 U.S.C. 154(b) by 403 days.

(21) Appl. No.: 12/663,156

(22) PCT Filed: Jun. 4, 2008

(86) PCT No.: PCT/JP2008/060269
§ 371 (c)(1),
(2), (4) Date: Dec. 4, 2009

(87) PCT Pub. No.: WO2008/149887
PCT Pub. Date: Dec. 11, 2008

(65) Prior Publication Data
US 2010/0163053 A1  Jul. 1, 2010

(30) Foreign Application Priority Data
Jun. 6, 2007  (JP) .................................. 2007-149912

(51) Int. Cl.
*A61F 6/06* (2006.01)
*A61F 13/15* (2006.01)
*A61F 5/24* (2006.01)
(52) U.S. Cl. ................... 128/830; 604/385.17; 128/97.1
(58) Field of Classification Search ............ 604/385.17, 604/904, 317, 358, 385.01, 385.18, 347, 604/353; 128/846, 885, 886, DIG. 25, 97.1, 128/100.1, 98.1, 99.1, 96.1, 105.1, 106.1; 600/38, 39, 40, 41, 29; 602/67, 68, 69, 70, 602/71, 73
See application file for complete search history.

(56) References Cited

U.S. PATENT DOCUMENTS

| | | | | |
|---|---|---|---|---|
| 3,116,734 A | * | 1/1964 | Terman | 604/329 |
| 3,554,184 A | * | 1/1971 | Habib | 600/29 |
| 4,484,919 A | * | 11/1984 | Sohn et al. | 604/358 |
| 4,615,692 A | * | 10/1986 | Giacalone et al. | 604/94.01 |
| 6,129,083 A | * | 10/2000 | Jansen | 128/846 |
| 2004/0024376 A1 | * | 2/2004 | Ohba | 604/385.17 |

FOREIGN PATENT DOCUMENTS

JP         09220253      *  8/1997

* cited by examiner

*Primary Examiner* — Loan Thanh
*Assistant Examiner* — Tarla Patel
(74) *Attorney, Agent, or Firm* — Maier & Maier PLLC (57) ABSTRACT

It is intended to prevent a pelvic organ from slipping out of the body by pushing up the organ having slipped out or just before slipping out. A device for preventing and treating pelvic organ prolapse characterized by comprising a convex push-up member which is made of a flexible material showing a pressing force toward a pelvic organ prolapse site of a wearer and in which the surface to be in contact with the pelvic organ is coated with a coating sheet, or a concave member which is made of a flexible material receiving the pelvic organ prolapse site and in which the surface to be in contact with the pelvic organ is coated with a coating sheet, and a means of holding the convex push-up member or the concave member for tightly pressing the convex push-up member or the concave member to the pelvic organ prolapse site of the wearer as described above.

21 Claims, 10 Drawing Sheets

EQUIPMENT FOR PREVENTING AND TREATING PELVIC ORGAN PROLAPSE

CROSS-REFERENCE TO RELATED APPLICATION

This application is a National Stage entry of International Stage entry of International No. PCT/JP2008/060269, filed Jun. 4, 2008, which claims priority to Japanese Patent Application No. 2007-149912, filed Jun. 6, 2007, the disclosure of the prior application is incorporated in its entirety by reference.

TECHNICAL FIELD

The present invention relates to an equipment for preventing and treating pelvic organ prolapse.

BACKGROUND ART

Pelvic organ prolapse is known as a disease with a symptom that one or more organs placed in a pelvis, such as an uterus, an urinary bladder, an urethra, a small intestine, and a rectum, drop into vagina and slip out from a female genital with a vaginal wall.

Pelvic organ prolapse may also called "uterine prolapse", "cystocele", "urethrocele", "enterocele", or "rectocele" depending on the slipping organ. Collectively, they are called "pelvic organ prolapse (genital prolapse)".

In general, pelvic organ prolapse is regarded as not being life-threatening.

However, the slipping out of pelvic organ(s) from vagina may cause a drying in the air, an abrasion, and even a bleeding of mucous membrane, thereby making it difficult for a patient to walk. Particularly, the slipping out of an urinary bladder affects an urethra and causes a certain symptom such as urinary incontinence or difficulty of urination. In addition, the slipping out of a rectum may cause difficulty in defecating. Thus, pelvic organ prolapse is one of so-called QOL (Quality Of Life) diseases which may cause a great deal of discomfort and distress in the patient's daily life. It is said that pelvic organ prolapse is a very common condition, particularly among postmenopausal women, and it is estimated in abroad that half of women aged 50 or over will experience some form of prolapse.

It is thought to be causally related to this disease that pelvic floor muscles supporting pelvic organs (an uterus, an urinary bladder, an urethra, a small intestine, and a rectum) become weak, loose or damaged mainly due to childbirth and can no longer support the pelvic organs. The other cases are seen in a situation where a chronic abdominal pressure is applied in case of asthma, hay fever, occupational standing work, engagement in agriculture, yard work, some kind of sport, constipation, obesity, or the like.

Pelvic organ prolapse is classified into first to fourth grades depending on how far the pelvic organ has fallen, each defined as dropping into vagina (stage I), reaching to vaginal opening (stage II), partly slipping out from vagina (stage III), and entirely slipping out from vagina (stage IV).

There have been known two method for treating pelvic organ prolapse; (1) one is a curative treatment by surgical operation; and (2) the other is a treatment by using a ring pessary.

The surgical operations of (1) includes: anterior vaginal wall plasty, vaginal total hysterectomy, posterior vaginal wall plasty, Manchester operation, sacrospinous ligament fixation of vaginal apex, musculus iliococcygeus fasciodesis (Inmon procedure), and sacrouterine ligament fixation (McCall technique), as vaginal operation; abdominal sacrocolpopexy as abdominal operation; laparoscopic sacrocolpopexy as laparoscopic operation; and Le Fort operation as colpocleisis. In addition, most recently, as an operation method enabling to reduce relapse rate, TVM (Tension free Vaginal Mesh) procedure using a gynemesh is proposed.

The ring pessary of (2) is provided as a toroidal shaped ring to be inserted into vagina. The ring pessary prevents the organs to drop by lifting up vagina.

DISCLOSURE OF INVENTION

Problems to be Solved by the Invention

Although the above-mentioned operations are required for a curative treatment, there are a lot of patients to whom the operations are improper because they hope to give birth or have physiological problems.

On the other hand, the treatment by using a pessary requires a foreign material to be inserted into vagina. Therefore, the pessary as a foreign material may induce an infection, thereby increasing vaginal discharge with a bad odor. Or the using of a pessary may cause an abrasion and a bleeding of mucous membrane and make it difficult to have a sexual intercourse. In addition, there are many cases that pessaries are not adaptable due to abnormality of form or size of vagina.

Meanwhile, many women wear tight corsets in order to keep their well-proportioned body lines. However, wearing tight corset may increase abdominal pressures, thereby aggravating the symptoms of pelvic organ prolapse.

Accordingly, it is an object of the present invention to provide a technique which enables to prevent and treat pelvic organ prolapse by pushing up the pelvic organ(s) having slipped out or just before slipping out.

Means for Solving the Problems

According to the present invention, there is provided an equipment for preventing and treating pelvic organ prolapse. The summary of the present invention will be described hereinafter.

(1) In accordance with an aspect of the present invention, there is provided an equipment for preventing and treating pelvic organ prolapse, comprising: a convex push-up member giving a pressing force toward a pelvic organ prolapse site of a wearer; and a holding mechanism for pressing the convex push-up member to the pelvic organ prolapse site of the wearer such that the convex push-up member is in close contact with the pelvic organ prolapse site.

(2) In accordance with an another aspect of the present invention, there is provided an equipment for preventing and treating pelvic organ prolapse, comprising: a convex push-up member which is made of a flexible material giving a pressing force toward a pelvic organ prolapse site of a wearer; and a holding mechanism for pressing the convex push-up member to the pelvic organ prolapse site of the wearer such that the convex push-up member is in close contact with the pelvic organ prolapse site.

(3) In accordance with a yet another aspect of the present invention, there is provided an equipment for preventing and treating pelvic organ prolapse, comprising: a convex push-up member which is made of a flexible material giving a pressing force toward a pelvic organ prolapse site of a wearer; a supporting member for supporting the convex push-up member; an adhesive or exchangeable sheet covering a surface of the convex push-up member to be contacted with a pelvic organ;

and a holding mechanism for pressing the convex push-up member to the pelvic organ prolapse site of the wearer.

(4) In the equipment for preventing and treating pelvic organ prolapse as recited in either one of (1) to (3), the convex push-up member may have a convex portion with a homogeneously filled structure or an opened or a closed cavity.

(5) In the equipment for preventing and treating pelvic organ prolapse as recited in (3) or (4), the supporting member may be homogeneously integrated with the convex push-up member or adhesive and heterogeneously integrated with the convex push-up member.

(6) In the equipment for preventing and treating pelvic organ prolapse as recited in either one of (3) to (5), the supporting member may be made of a material with hardness enough to maintain a form of the convex push-up member.

(7) In the equipment for preventing and treating pelvic organ prolapse as recited in either one of (3) to (6), the covering sheet may further cover the supporting member.

(8) In the equipment for preventing and treating pelvic organ prolapse as recited in either one of (1) to (7), the convex push-up member may have a shape as either one of hemisphere, sphere, oval hemisphere, oval sphere, or egg-shape.

(9) In the equipment for preventing and treating pelvic organ prolapse as recited in either one of (3) to (8), the covering sheet may be made of either one of gel, textile, or deodorant textile.

(10) In accordance with a further aspect of the present invention, there is provided an equipment for preventing and treating pelvic organ prolapse, comprising: a concave member receiving a pelvic organ prolapse site of a wearer; and a holding mechanism for pressing the concave member to the pelvic organ prolapse site of the wearer such that the concave member is in close contact with the pelvic organ prolapse site.

(11) In accordance with a still further aspect of the present invention, there is provided an equipment for preventing and treating pelvic organ prolapse, comprising: a concave member which is made of a flexible material so as to receive a pelvic organ prolapse site of a wearer; and a holding mechanism for pressing the concave member to the pelvic organ prolapse site of the wearer such that the concave member is in close contact with the pelvic organ prolapse site.

(12) In accordance with a yet further aspect of the present invention, there is provided an equipment for preventing and treating pelvic organ prolapse, comprising: a concave member which is made of a flexible material so as to receive a pelvic organ prolapse site of a wearer; a supporting member for supporting the concave member; an adhesive or exchaneable covering sheet covering an inner surface of the concave member; and a holding mechanism for pressing the concave member to the pelvic organ prolapse site of the wearer.

(13) In the equipment for preventing and treating pelvic organ prolapse as recited in (12), the supporting member may be homogeneously integrated with the concave member or heterogeneously and adhesively integrated with the concave member.

(14) In the equipment for preventing and treating pelvic organ prolapse as recited in (12) or (13), the supporting member may be made of a material with hardness enough to maintain a form of the concave member.

(15) In the equipment for preventing and treating pelvic organ prolapse as recited in either one of (12) to (14), the covering sheet may further cover the supporting member.

(16) In the equipment for preventing and treating pelvic organ prolapse as recited in either one of (12) to (15), the covering sheet may be made of either one of gel, textile, or deodorant textile.

(17) In the equipment for preventing and treating pelvic organ prolapse as recited in either one of (10) to (16), the concave member may have a shape as either one of hemisphere, sphere, oval hemisphere, oval sphere, or egg-shape.

(18) In the equipment for preventing and treating pelvic organ prolapse as recited in either one of (1) to (17), the convex push-up member or the concave member may be made of a material having a shape-memory effect.

It is to be noted that the material having a shape-memory effect may be provided as a synthetic fiber fabric, a synthetic resin, an alloy, or the like.

(19) In the equipment for preventing and treating pelvic organ prolapse as recited in either one of (1) to (18), the holding mechanism may comprise: an adapter to which the convex push-up member or the concave member is attached and removable such that the convex push-up member or the concave member is located at an adjustable position with respect to the pelvic organ prolapse site; a waist belt to be worn around a waist of the wearer, the waist belt having an adjustable length thereof and being easily removable; and a holding belt for connecting the adapter to the waist belt and pushing up and holding the convex push-up member or the concave member toward the pelvic organ prolapse site of the wearer, the holding belt having an adjustable length thereof.

(20) In the equipment for preventing and treating pelvic organ prolapse as recited in (19), the holding belt may comprise first and second holding belts, the adapter has a front-side opening located at a front side of the adapter and a rear-side opening located at a rear side of the adapter, the first holding belt has a first end connected to a first front-side position at a front side of the waist belt and a second end connected to a first rear-side position at a rear side of the waist belt such that the first holding belt passes through the front-side opening and the rear-side opening, and the second holding belt has a first end connected to a second front-side position different from the first front-side position at the front side of the waist belt and a second end connected to a second rear-side position different from the first rear-side position at the rear side of the waist belt such that the second holding belt passes through the front-side opening and the rear-side opening.

(21) In the equipment for preventing and treating pelvic organ prolapse as recited in (19) or (20), the adapter may be located at an adjustable position with respect to the holding belt.

(22) In the equipment for preventing and treating pelvic organ prolapse as recited in either one of (1) to (18), the holding mechanism may include a sheet member, the sheet member and a bottom portion of an underwear form a sack having a single-sided opening, and the convex push-up member or the concave member is placed in the single-sided opening.

Advantageous Effect of the Invention

The present invention provides an equipment which has a convex push-up member giving a pressing force toward a pelvic organ prolapse site or a concave member receiving the same, and a holding mechanism for pressing the convex push-up or concave member to the pelvic organ prolapse site. Therefore, it becomes possible to provide a technique which enables to prevent and treat pelvic organ prolapse by pushing up the pelvic organ(s) having slipped out or just before slipping out. For example, since the convex push-up member or concave member ensures a certain volume in vagina as a closed space, the pelvic organs are prevented from slipping out from vagina.

DESCRIPTION OF REFERENCE NUMERALS

100A; convex push-up member having a convex portion with a homogeneously or heterogeneously filled structure
100B; convex push-up member having a convex portion with an opened cavity
100C; convex push-up member having a convex portion with a closed cavity
100D; concave member
1; convex portion made of a flexible material
2; supporting member
2A; supporting member having a hardness enough to maintain the shape of the convex portion
3; covering sheet for adhesive or exchangeable covering
4; opened cavity of the convex portion
5; closed cavity of the convex portion
6; adjuster
7; waist belt
8; adjuster
8A and 8B; positions to each of which a holding belt is connected
9; adapter
10; opening
11; holding belt
12; D-rings
13; underwear for woman

BEST MODE FOR CARRYING OUT THE INVENTION

Hereinafter, embodiments of the present invention will be described with reference to the drawings.

In the following embodiments of the present invention, like reference numerals designate like parts throughout the figures, and repeated description thereof will be omitted.

Figure 1:
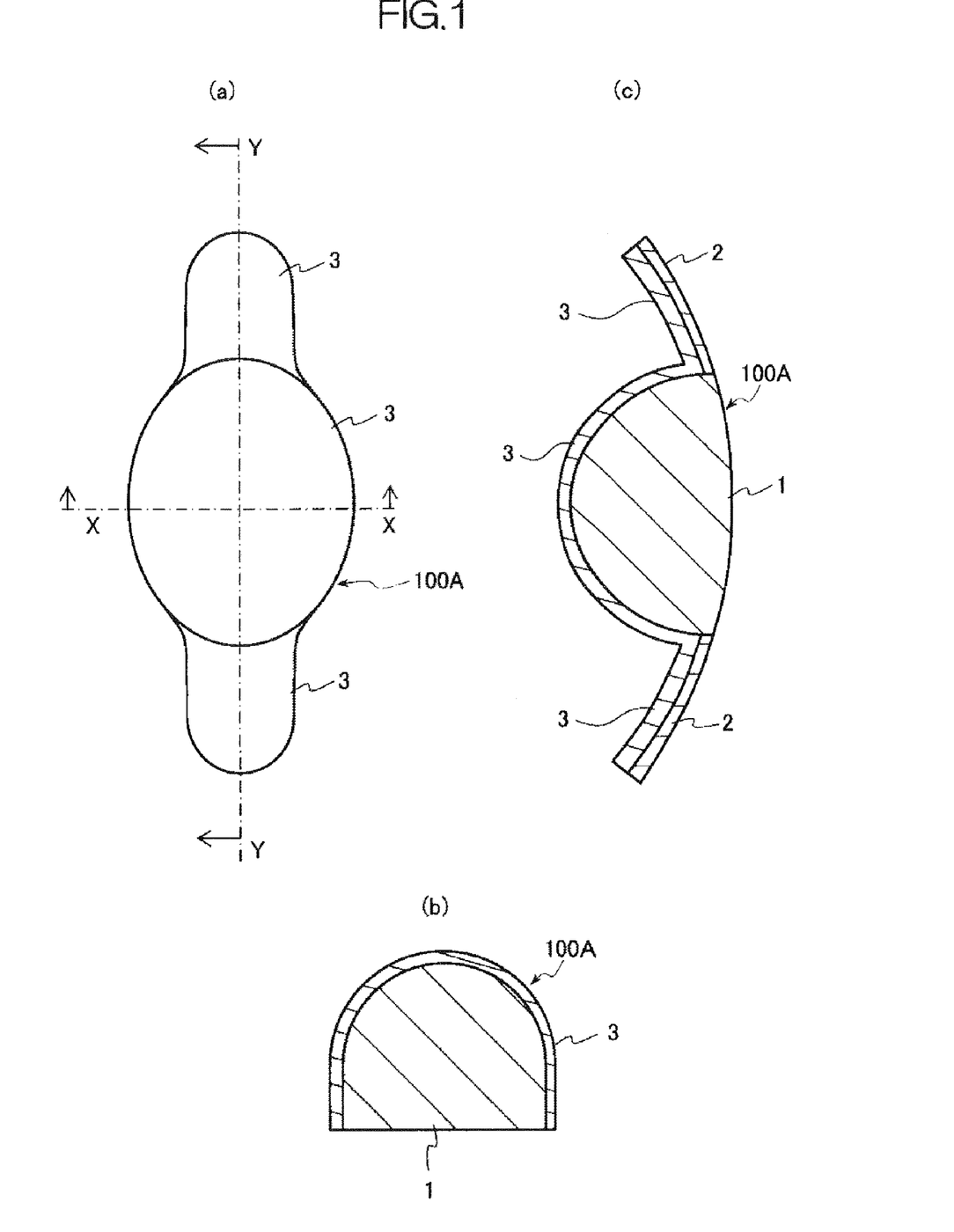
FIG. 1 schematically illustrates a convex push-up member having a convex portion with a homogeneously or heterogeneously filled structure according to an embodiment of the present invention.
Figure 2:
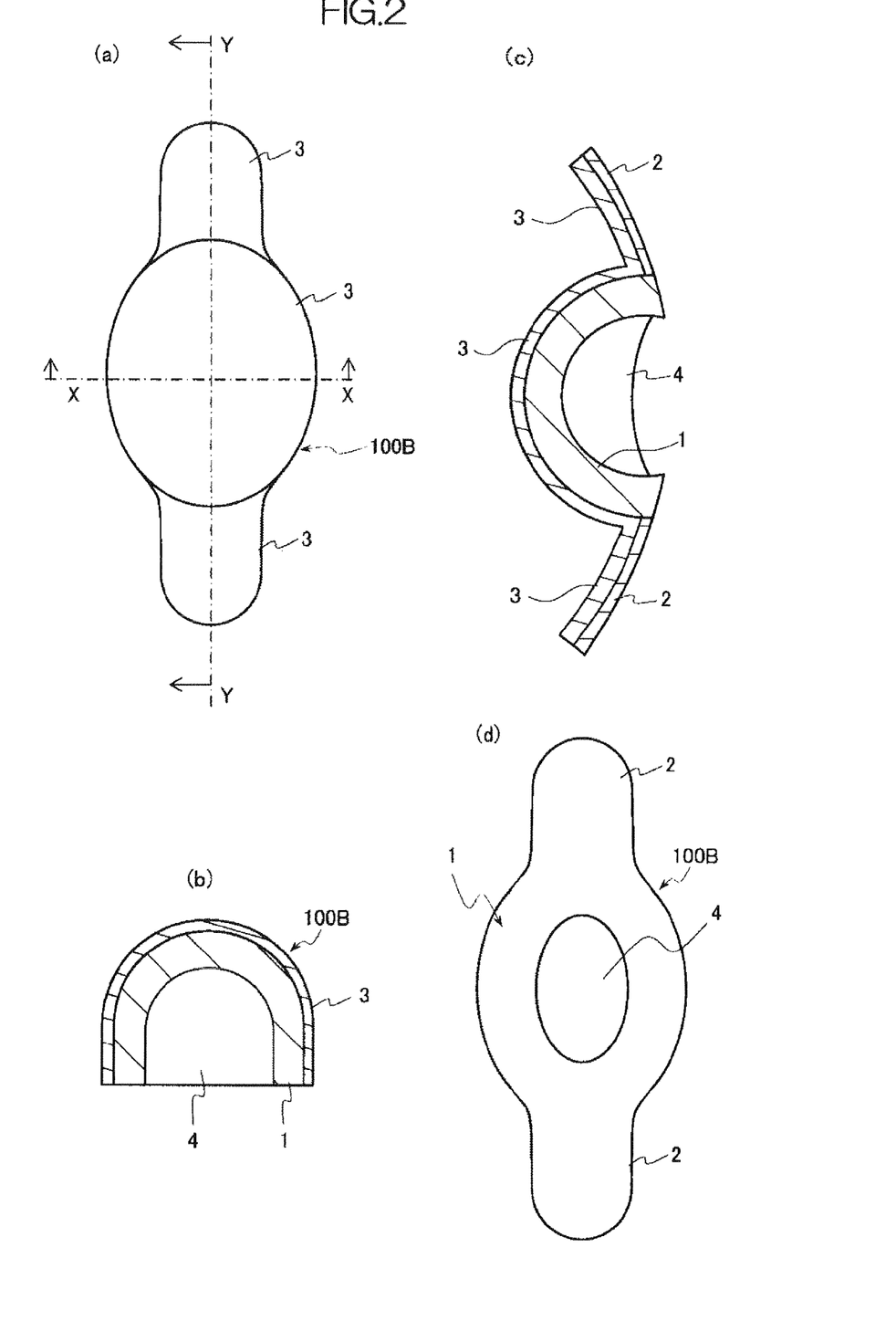
FIG. 2 schematically illustrates a convex push-up member having a convex portion with an opened cavity according to an another embodiment of the present invention.
Figure 3:
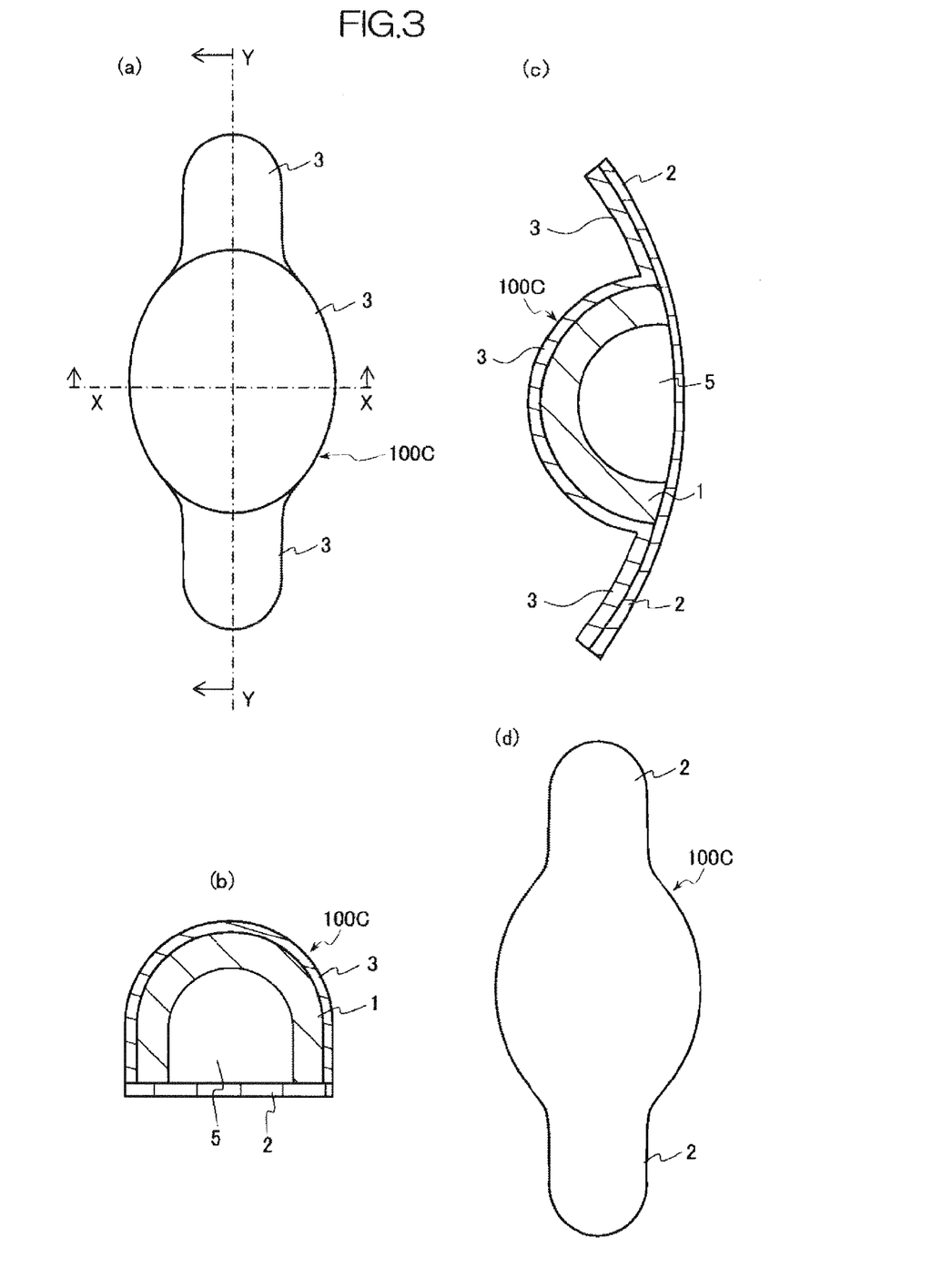
FIG. 3 schematically illustrates a convex push-up member having a convex portion with a closed cavity according to a still another embodiment of the present invention.

FIGS. 1 to 3 schematically illustrate convex push-up members 100A, 100B, and 100C according to the embodiments of the present invention, respectively. The convex push-up member 100A shown in FIG. 1 has a convex portion 1 with a homogeneously filled structure. The convex push-up member 100B shown in FIG. 2 has a convex portion 1 with an opened cavity 4. The convex push-up member 100C shown in FIG. 3 has a convex portion 1 with a closed cavity 5.

In each of FIGS. 1 to 3, (a) illustrates a plan view, (b) illustrates a cross-sectional view along with the line X-X shown in (a), and (c) illustrates a cross-sectional view along with the line Y-Y shown in (a), and in each of FIGS. 2 and 3, (d) illustrates a rear view.

Alternatively, the convex push-up member 100A shown in FIG. 1 may have a convex portion 1 with a heterogeneously filled structure.

The structure shown in each of FIGS. 1 to 3 further has a supporting member 2 for supporting the convex portion 1 and a covering sheet 3 adhesively or exchangeably covering a surface of the convex portion 1 to be contacted with a pelvic organ. Particularly in the present embodiments, the covering sheet 3 further covers the supporting member 2. In addition, each convex portion 1 of the convex push-up members 100A, 100B, and 100C is made of a flexible material giving a pressing force toward a pelvic organ prolapse site of a wearer. The flexible material may be provided as, for example, a natural fiber, a chemical fiber, a synthetic fiber, a synthetic rubber, or the like. Although not intended to limit the present invention, a natural rubber may be restricted to be used as the flexible material because there is a possibility that a natural rubber causes skin problems.

Thus, the equipment for preventing and treating pelvic organ prolapse each according to the present embodiments of the present invention is characterized in that, as shown in either one of FIGS. 1 to 3, the convex push-up member 100A, 100B, or 100C has a convex portion 1 made of a flexible material giving a pressing force toward a pelvic organ prolapse site of a wearer, and that the surface of the convex portion 1 to be contacted with a pelvic organ is covered by a covering sheet 3. The convex portion 1 of the convex push-up member 100A, 100B, or 100C is held by a holding mechanism in a situation where the covering sheet 3 is close contacted with the pelvic organ prolapse site. The holding mechanism will be described later.

It is to be noted that the covering sheet 3 is not essential in the present invention. The covering sheet 3 may be used as necessary.

The supporting member 2 is homogeneously integrated with the convex portion 1 of the convex push-up member 100A, 100B, or 100C. Alternatively, the supporting member 2 may be adhesive and heterogeneously integrated with the convex portion 1 of the convex push-up member 100A, 100B, or 100C. Preferably, the convex portion 1 has a shape as either one of hemisphere, sphere, oval hemisphere, oval sphere, or egg-shape. As described above, the flexible material forming the convex portion 1 may be made of a synthetic rubber. For example, the convex portion 1 is formed of a silicone rubber having hardness between approximately 10 degrees to 40 degrees. Such silicone rubber provides an optimum touchably-smoothness and an appropriate flexibility and elasticity, thereby allowing the convex portion 1 to have an optimum pressing force toward a pelvic organ prolapse site.

Figure 4:
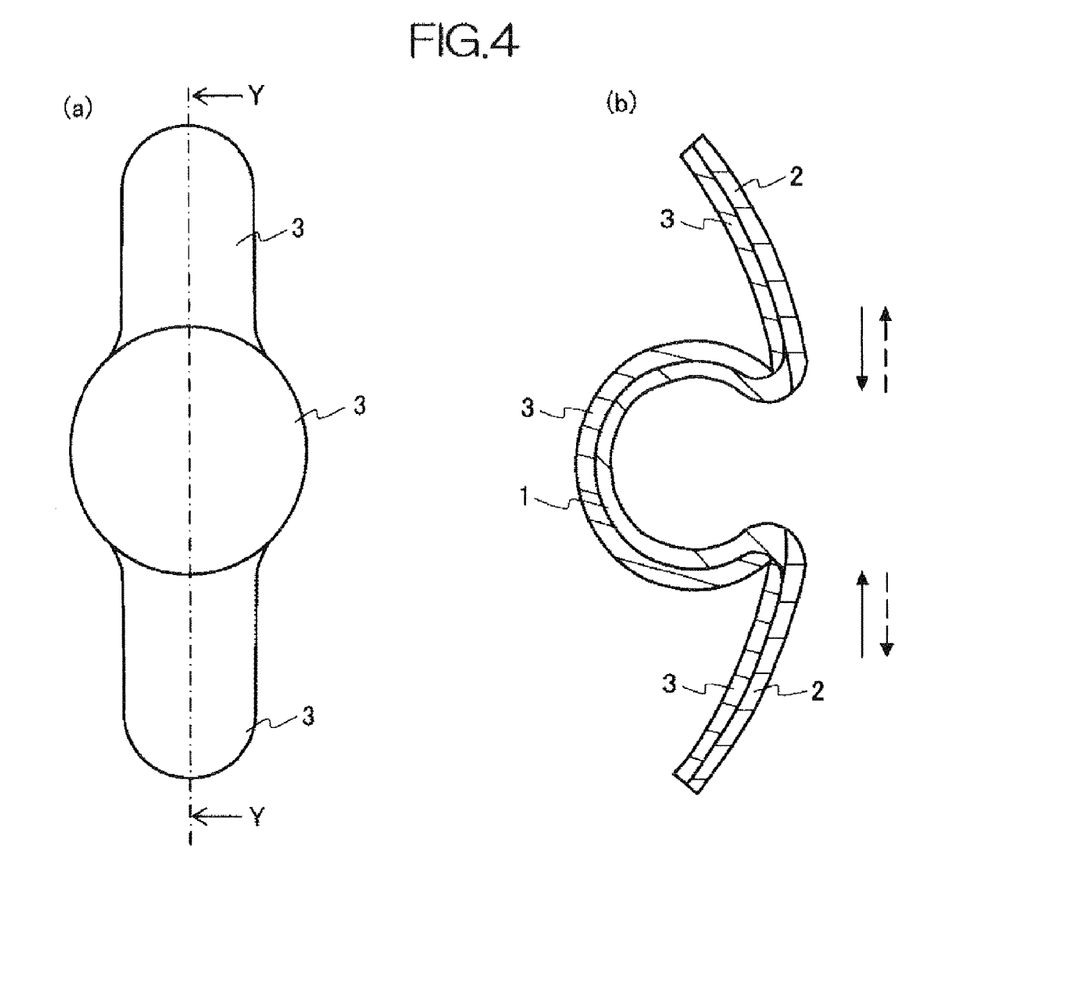
FIG. 4 represents a plan view (a) and a cross-sectional view (b) schematically illustrating a structure of clip-type with a function of the convex portion according to a yet another embodiment of the present invention.
Figure 5:
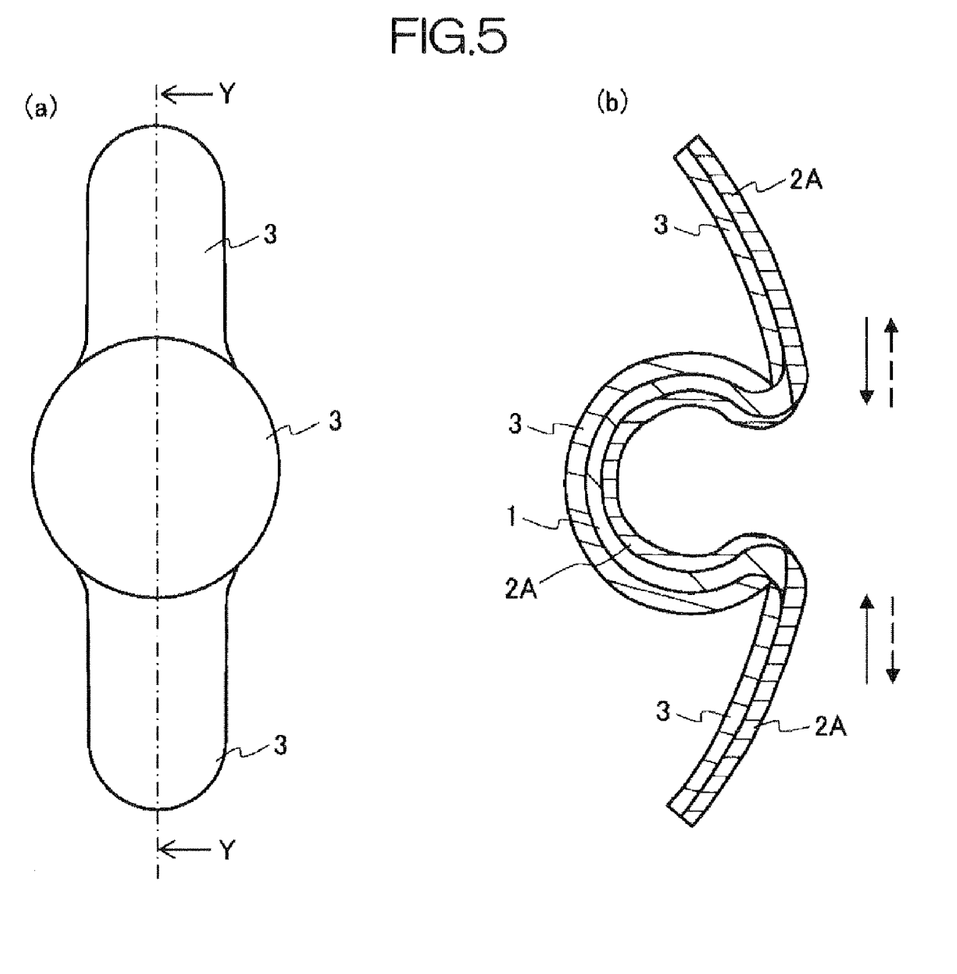
FIG. 5 represents a plan view (a) and a cross-sectional view (b) schematically illustrating an improvement of the structure of clip-type shown in FIG. 4.

FIGS. 4 and 5 each schematically illustrates another embodiment of the present invention, where (a) illustrates a plan view, and (b) illustrates a cross-sectional view along with the line Y-Y shown in (a). The embodiment shown in FIG. 4 is characterized in that the convex portion 1 is formed in a thin shape relatively to the embodiments shown in FIGS. 1 to 3. As a result, the convex portion 1, the supporting member 2, and the covering sheet 3 shown in FIG. 4 may function on a whole as a clip. That is, after grasping the upper end and the lower end of the supporting member 2 by a hand in directions shown by solid arrows, in this situation inserting the convex portion 1 covered by the covering sheet 3 into a vagina, and releasing the supporting member 2, the convex portion 1 stretches out by its own elastic force as shown by dashed arrows, and the convex portion 1 establishes the position thereof in the vagina.

Figure 6:
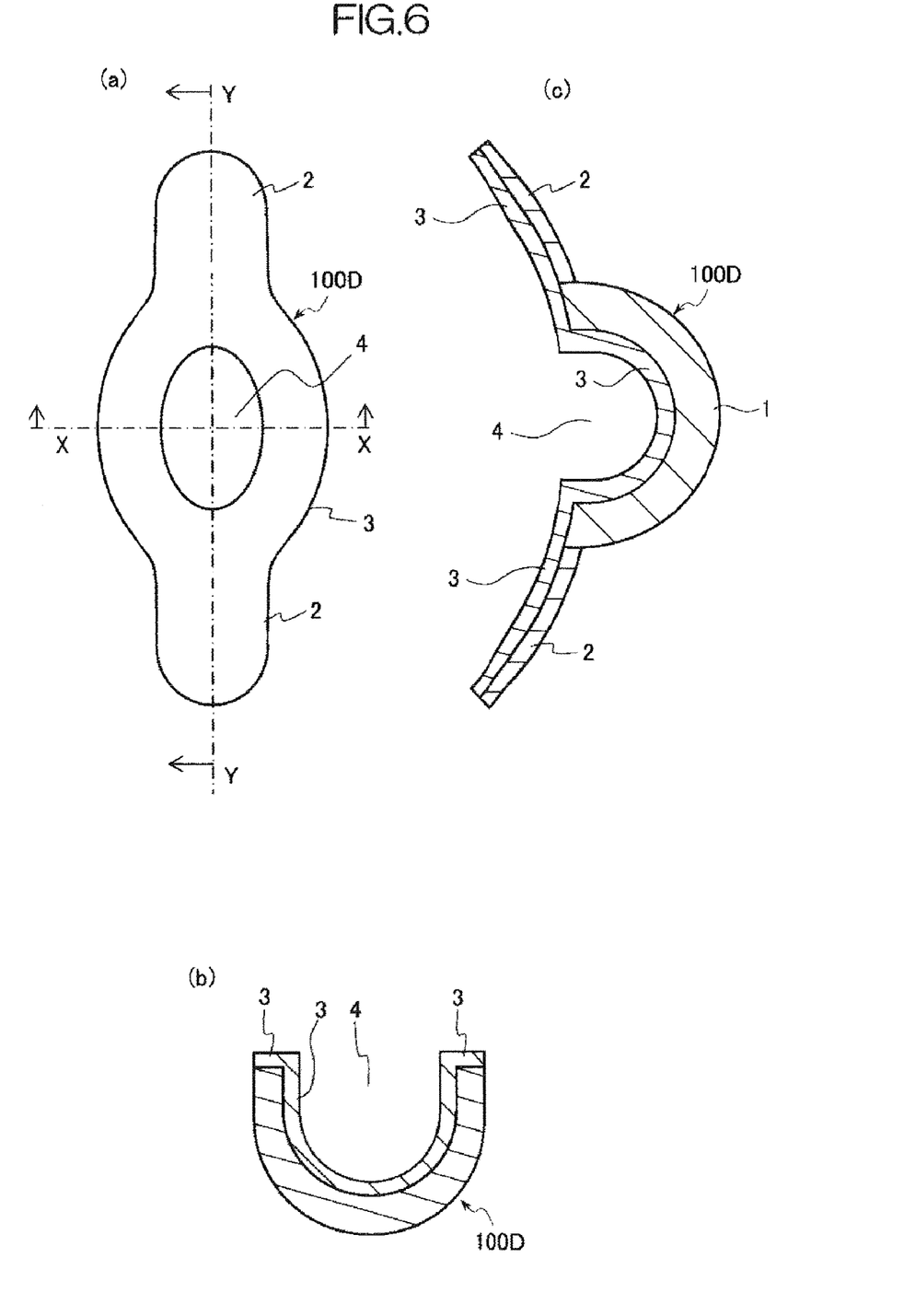
FIG. 6 schematically illustrates a concave member according to a further embodiment of the present invention.

FIG. 6 schematically illustrates a further embodiment of the present invention, where (a) illustrates a plan view, (b) illustrates a cross-sectional view along with the line X-X shown in (a), and (c) illustrates a cross-sectional view along with the line Y-Y shown in (a). This embodiment will be described later.

The embodiment shown in FIG. 4 has a spherical shape of the convex portion 1. Therefore, when the wearer closes her legs, it may be difficult to maintain the shape of the convex portion 1 because the convex portion 1 is subject to sideways pressures. As a result, the deformation of the convex portion 1 may bring discomfort for the wearer. In order to avoid this, according to the embodiment shown in FIG. 5, there is provided a supporting member 2A having a hardness enough to maintain the shape of the convex portion 1 as substitute for the supporting member 2. Although not limited, the convex portion 1 is placed between a part of the supporting member 2A and a part of the covering sheet 3 in the present embodiment. The supporting member 2A is, for example, formed of a silicone rubber having hardness between approximately 40 degrees to 80 degrees.

In the embodiment shown in FIG. 5, after grasping the upper end and the lower end of the supporting member 2A by a hand in directions shown by solid arrows, in this situation inserting into a vagina the convex portion 1 covered outside thereof by the covering sheet 3 and inside thereof by the supporting member 2A, and releasing the supporting member 2A, the convex portion 1 stretches out by its own elastic force with assistance by the supporting member 2A as shown by dashed arrows, and the convex portion 1 establishes the position thereof in the vagina. Especially in the present embodiment, the supporting member 2A supports and covers the convex portion 1 so as to maintain the shape of the convex portion 1. Accordingly, when the convex portion 1 is inserted in a vagina, elastic force thereof acts such that the convex portion 1 is placed in the vagina, thereby preventing the convex portion 1 to slip out from the vagina.

Through the embodiments of the present invention, the covering sheet 3 may be made of gel, textile, deodorant textile, or the like, and may adhesively or exchangeably cover a surface of the convex push-up member 100A, 100B, or 100C to be contacted with a pelvic organ.

In addition, it is effective for comfort to form the convex portion 1 and the supporting members 2 and 2A of deodorant materials. For example, the deodorant material may be obtained by mixing deodorant powder, such as activated charcoal, bamboo charcoal, and wood charcoal into a base material. Alternatively, deodorant powder or the like may be sealed into a cavity formed in the base material. It is to be noted that most suitable one is selected from the convex push-up member 100A, 100B, or 100C and used in accordance with the symptom of pelvic organ prolapse.

Referring to FIG. 6, there is shown a further embodiment of the present invention where a concave member 100D is used in place of the convex push-up members 100A, 100B, and 100C. The concave member 100D may be provided by reversing the convex push-up member 100B and applying the covering sheet 3 to an inner surface of the concave member 100D (that is the reversed convex push-up member 100B). In this case, the opened cavity 4 is formed in the concave member 100D.

Thus, the equipment for preventing and treating pelvic organ prolapse according to the embodiment shown in FIG. 6 comprises the concave member 100D which is made of a flexible material so as to receive a pelvic organ prolapse site of a wearer, the supporting member 2 for supporting the concave member 100D, the adhesive or exchangeable covering sheet 3 covering the inner surface of the concave member 100D, and a holding mechanism for pressing the concave member to the pelvic organ prolapse site of the wearer. Particularly in the present embodiment, the pelvic organ prolapse site of the wearer is received by the opened cavity which is defined by the concave member 100D and the covering sheet 3 applied to the inner surface of the concave member 100D.

Although not limited, the covering sheet 3 may further cover the supporting member 2 as a structure shown in the drawings. This structure enables the adhesive or connective portion between the convex push-up member 100A, 100B, or 100C, or the concave member 100D and the supporting member 2 to be strengthened.

The convex push-up member 100A, 100B, or 100C, or the concave member 100D may be made of a material having a shape-memory effect. The material having a shape-memory effect may be provided as a synthetic fiber fabric, a synthetic resin, an alloy, or the like. According to this embodiment, the material having a shape-memory effect allows the wearer to define the shape of the convex push-up member 100A, 100B, or 100C, or the concave member 100D, thereby removing uncomfortable feeling or pain from the wearer. Therefore, pelvic organ prolapse may be prevented or treated with less stress for the wearer.

Hereinafter, the holding mechanism applicable to the convex push-up member 100A, 100B, or 100C, or the concave member 100D will be described in detail.

Figure 7:
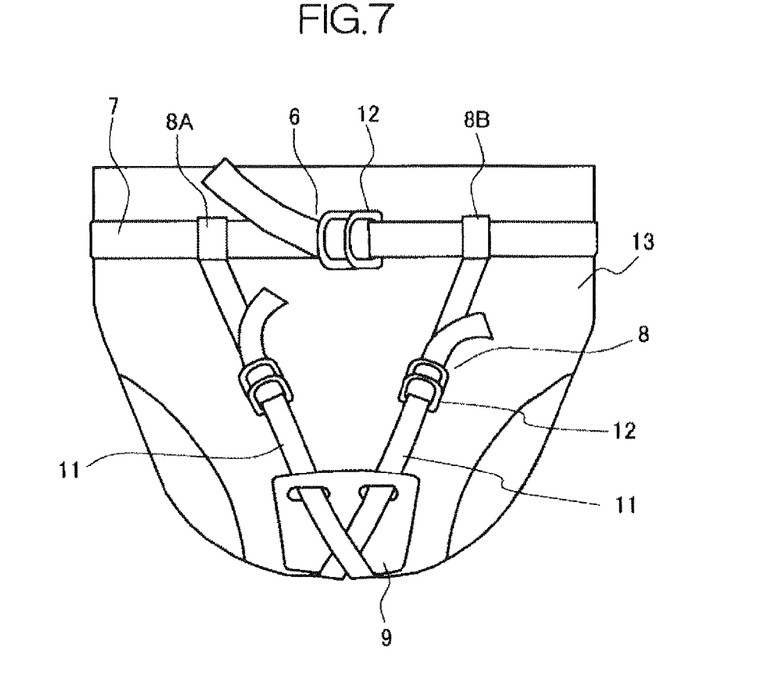
FIG. 7 is a front elevated view illustrating a holding mechanism for pressing the convex push-up member (or the convex member) to a pelvic organ prolapse site, which is applicable to embodiments of the present invention.
Figure 8:
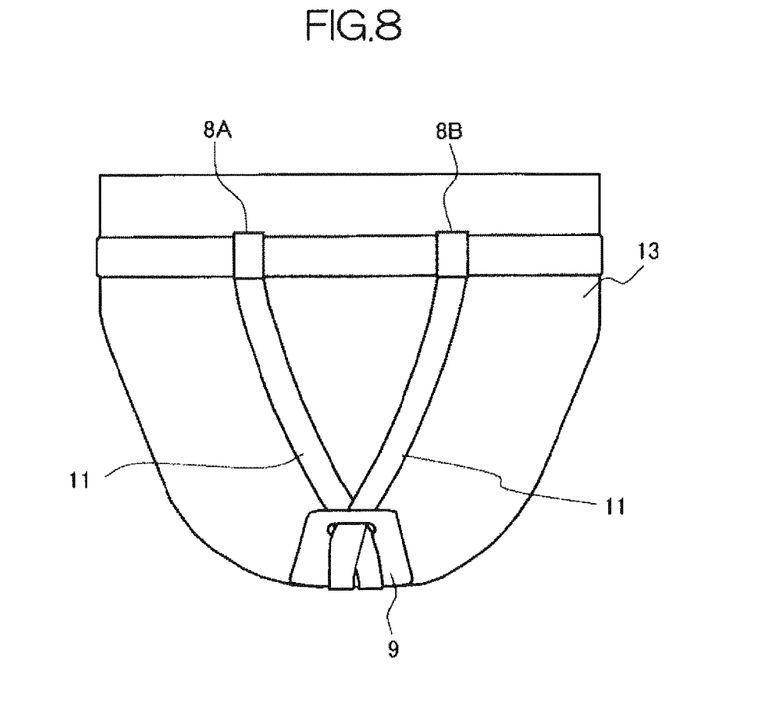
FIG. 8 is a back elevated view illustrating the holding mechanism shown in FIG. 7.

FIG. 7 is a schematic front elevational view illustrating the holding mechanism according to the embodiments of the present invention, to which the convex push-up member 100A, 100B, or 100C, or the concave member 100D is attached and removable at an adjustable position, and FIG. 8 is a schematic back elevated view of the holding mechanism shown in FIG. 7.

The holding mechanism includes a waist belt 7 to be worn around a waist of a wearer. More specifically, the waist belt 7 is wound around an outer circumference of an underwear 13 in the vicinity of a hipbone of the wearer. The waist belt 7 has an adjuster 6 for adjusting the winding length thereof. As the adjuster 6, D-rings 12 or the like may be used. Such D-rings 12 allow the waist belt 7 to be easily removable.

Reference numeral 9 denotes an adapter to which the convex push-up member 100A, 100B, or 100C, or the concave member 100D is removably attached at an adjustable position. The adapter 9 is connected to the waist belt 7 by means of a holding belt. Especially in the present invention, the holding belt comprises first and second holding belts 11 and 11. Each holding belt 11 has an adjuster 8 for adjusting the length thereof. As the adjuster 8, D-rings 12 or the like may be used. Such D-rings 12 allow the wearer to easily attach and remove the adapter 9.

The adapter 9 and the holding belts 11 and 11 are provided for pushing up and holding either one of the convex push-up member 100A, 100B, or 100C, or the concave member 100D toward the pelvic organ prolapse site of the wearer. The pressing force toward the pelvic organ prolapse site is adjustable by using the adjusters 8 and 8 of the holding belts 11 and 11.

Figure 9:
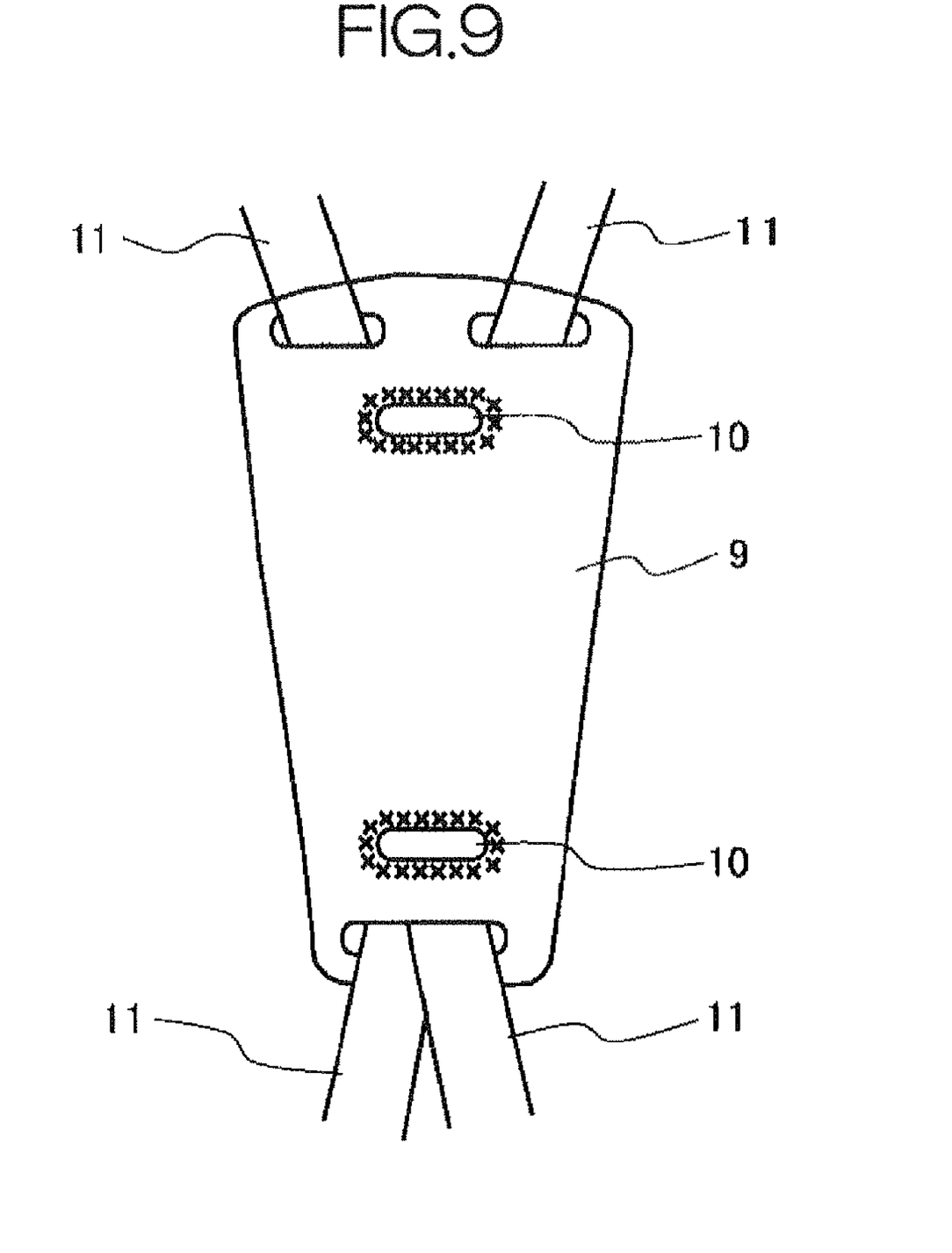
FIG. 9 is a plan view illustrating holding belts and an adapter shown in FIGS. 7 and 8 seen from the convex push-up member (or the concave member).
Figure 10:
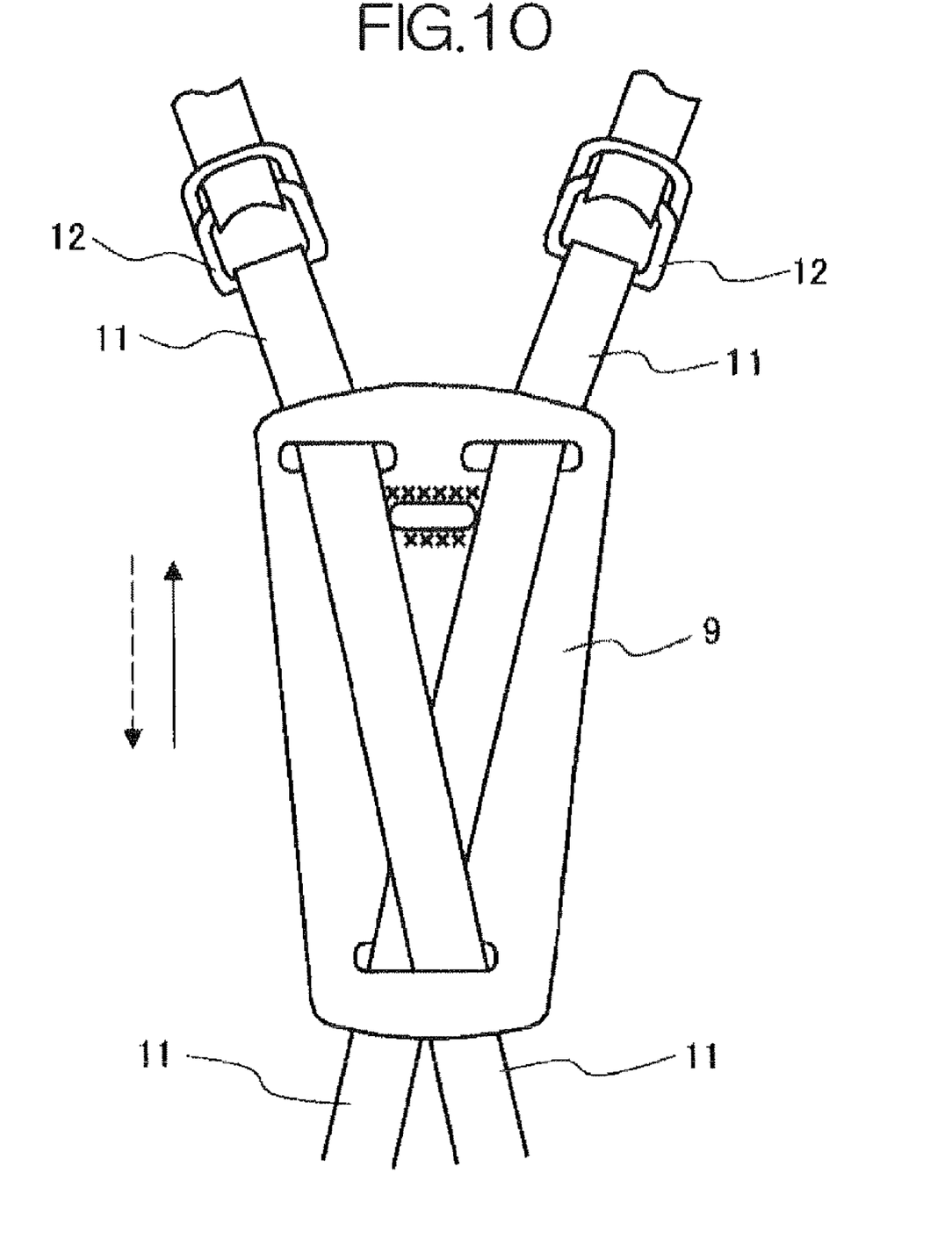
FIG. 10 is a bottom view illustrating the holding belts and the adapter shown in FIG. 9.

Referring to FIGS. 9 and 10 and taking the structure shown in FIGS. 7 and 8 into consideration, the adapter 9 has first and second front-side openings located at a front side of the adapter 9 and a rear-side opening located at a rear side of the adapter 9.

The first holding belt 11 (on the observers' left in FIG. 7) has a first end connected to a first front-side position 8A (on the observers' left in FIG. 7) at a front side of the waist belt 7 and a second end connected to a first rear-side position 8A (on the observers' left in FIG. 8) at a rear side of the waist belt 7 such that the first holding belt 11 passes through the first front-side opening (on the observers' right in FIG. 9) and the rear-side opening.

The second holding belt 11 (on the observers' right in FIG. 7) has a first end connected to a second front-side position 8B (in FIG. 7) different from the first front-side position 8A (in FIG. 7) at the front side of the waist belt 7 and a second end connected to a second rear-side position 8B (in FIG. 8) different from the first rear-side position 8A (in FIG. 8) at the rear side of the waist belt 7 such that the second holding belt 11 passes through the second front-side opening (on the observers' left in FIG. 9) and the rear-side opening.

It is to be noted that reference numerals 8A and 8B in FIG. 7 designate what are different from parts designated by same reference numerals in FIG. 8.

According to the present embodiment where the adapter 9 has two front-side openings (the first and second front-side openings), the first and second holding belts 11 and 11 cross to each other on or near the adapter 9, thereby preventing a deformation of the adapter 9 caused from tensions of the holding belts 11 and 11.

Although not shown, alternatively to having two front-side openings, the adapter 9 may have a single front-side opening to be shared by the first and second holding belts 11 and 11. In any way, according to the structure of the embodiments, the holding belts 11 and 11 hold the adapter 9 by passing through the openings, thereby allowing the adapter 9 to be located at an adjustable position with respect to the holding belts 11 and 11.

Alternatively to using the adapter 9, the holding mechanism may include a sheet member, such as a relatively hard fabric, a flexible resin sheet, or the like cooperating with an underwear. That is, the sheet member is provided such that the sheet member and the bottom portion of the underwear form a sack having a single-sided opening, and the convex push-up member 100A, 100B, or 100C, or the concave member 100D is placed in the single-sided opening. For example, when a rectangular fabric is used as the sheet member, the sack may be formed by sewing three sides of the rectangular fabric to the bottom of the underwear. The bottom of the underwear may be a crotch located below a pubic bone of the wearer. According to the embodiment, it becomes possible to provide a simple holding mechanism.

Referring again to FIGS. 9 and 10, the adapter 9 further has openings 10 and 10, and both ends of the supporting member 2 or 2A are inserted into the openings 10 and 10. According to the structure, the convex push-up member 100A, 100B, or 100C, or the concave member 100D may be attached and removable to the adapter 9 such that the convex push-up member 100A, 100B, or 100C, or the concave member 100D is located at an adjustable position with respect to the pelvic organ prolapse site. It is to be noted that the convex push-up member 100A, 100B, or 100C, or the concave member 100D may be selected in accordance with the grade of pelvic organ prolapse or individual variability.

Figure 11:
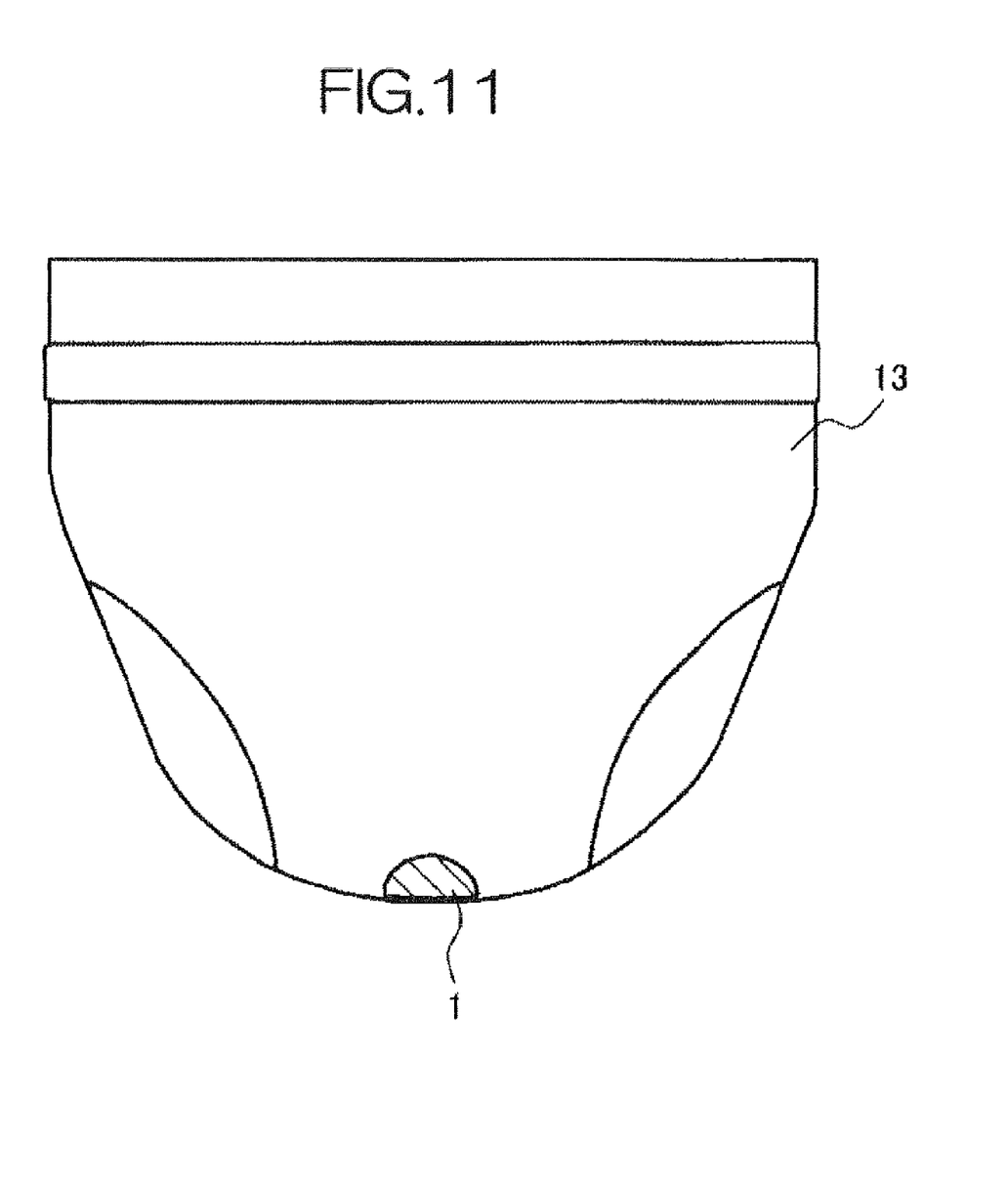
FIG. 11 is a schematic view illustrating an underwear with a function of the convex portion according to the embodiments of the present invention.

In addition, if symptoms are not severe, an underwear having a function as the convex push-up member 100A, 100B, or 100C, or the concave member 100D may be available for preventing or treating pelvic organ prolapse, as shown in FIG. 11.

As understood from the above description, the present invention provides an equipment which has a convex push-up member giving a pressing force toward a pelvic organ prolapse site or a concave member receiving the same, and a holding mechanism for pressing the convex push-up or concave member to the pelvic organ prolapse site. Therefore, it becomes possible to provide a technique which enables to prevent and treat pelvic organ prolapse by pushing up the pelvic organ(s) having slipped out or just before slipping out. For example, since the convex push-up member ensures a certain volume in vagina as a closed space, the pelvic organs are prevented from slipping out from vagina.

Particularly in the case that the convex push-up or concave member is made of a flexible material giving a pressing force toward the pelvic organ prolapse site, the pelvic organs may be free from stress or pain.

Moreover, by adapting an adhesive or exchangeable covering sheet covering a surface of the convex push-up or concave member to be contacted with a pelvic organ, it becomes possible to remove uncomfortable feeling or pain from the wearer.

Thus, the present invention provides an equipment for preventing and treating pelvic organ prolapse which allows women suffering from various symptoms of pelvic organ prolapse to live comfortably without inconvenience in their daily life.

INDUSTRIAL APPLICABILITY

The present invention is applicable to the industrial field in medical equipment, nursing care product, or the like.

The invention claimed is:

1. An equipment for preventing and treating pelvic organ prolapse, which is to be worn by a wearer so as to be in contact with a female genital, comprising:
   a member facing to the female genital; and
   a holding mechanism for holding the member such that the member is in close contact with the female genital of the wearer,
   wherein the holding mechanism comprises:
   an adapter to which the member is attached and removable such that the member is located at an adjustable position with respect to the female genital;
   a waist belt to be worn around a waist of the wearer, the waist belt having an adjustable length thereof and being easily removable; and
   a holding belt for connecting the adapter to the waist belt and pushing up and holding the member toward the female genital, the holding belt having an adjustable length thereof, and
   wherein the holding belt comprises first and second holding belts, the adapter has a front-side opening located at a front side of the adapter and a rear-side opening located at a rear side of the adapter, the first holding belt has a first end connected to a first front-side position at a front side of the waist belt and a second end connected to a first rear-side position at a rear side of the waist belt such that the first holding belt passes through the front-side opening and the rear-side opening, and the second holding belt has a first end connected to a second front-side position different from the first front-side position at the front side of the waist belt and a second end connected to a second rear-side position different from the first rear-side position at the rear side of the waist belt such that the second holding belt passes through the front-side opening and the rear-side opening.

2. The equipment for preventing and treating pelvic organ prolapse as recited in claim 1,
wherein the member is made of a flexible material formed of at least one of a natural fiber, a chemical fiber, a synthetic fiber, a synthetic rubber, and a synthetic resin.

3. The equipment for preventing and treating pelvic organ prolapse as recited in claim 1, further comprising:
a supporting member for supporting the member; and
an adhesive or exchangeable covering sheet covering a surface of the member to be contacted with the female genital or a pelvic organ slipping out from the female genital.

4. The equipment for preventing and treating pelvic organ prolapse as recited in claim 3, wherein the supporting member is homogeneously integrated with the member or heterogeneously and adhesively integrated with the member.

5. The equipment for preventing and treating pelvic organ prolapse as recited in claim 3, wherein the supporting member is made of a material with hardness enough to maintain a form of the member.

6. The equipment for preventing and treating pelvic organ prolapse as recited in claim 5, wherein the hardness of the supporting member is between 40 degrees and 80 degrees.

7. The equipment for preventing and treating pelvic organ prolapse as recited in claim 3, wherein the covering sheet further covers the supporting member.

8. The equipment for preventing and treating pelvic organ prolapse as recited in claim 3, wherein the covering sheet is made of either one of gel, textile, or deodorant textile.

9. The equipment for preventing and treating pelvic organ prolapse as recited in claim 1, wherein the holding mechanism includes an adapter to which the member is attached and removable such that the member is located at an adjustable position with respect to the female genital;
the adapter has openings; and
both ends of the supporting member are inserted into the openings.

10. The equipment for preventing and treating pelvic organ prolapse as recited in claim 1, wherein the member is made of a material having a shape-memory effect.

11. The equipment for preventing and treating pelvic organ prolapse as recited in claim 1, wherein the member has a shape as either one of hemisphere, sphere, oval hemisphere, oval sphere, or egg-shape.

12. The equipment for preventing and treating pelvic organ prolapse as recited in claim 1, wherein the member is a convex member giving a pressing force toward the female genital.

13. The equipment for preventing and treating pelvic organ prolapse as recited in claim 1, wherein the convex member has a convex portion with a homogeneously filled structure or an opened or a closed cavity.

14. The equipment for preventing and treating pelvic organ prolapse as recited in claim 1, wherein the member is a concave member receiving a pelvic organ slipping out from the female genital.

15. The equipment for preventing and treating pelvic organ prolapse as recited in claim 1, wherein the adapter is located at an adjustable position with respect to the first and second holding belts.

16. The equipment for preventing and treating pelvic organ prolapse as recited in claim 1, wherein the holding mechanism includes a sheet, the sheet and a bottom portion of an underwear form a sack having a single-sided opening, and the member is placed in the single-sided opening.

17. The equipment for preventing and treating pelvic organ prolapse as recited in claim 1, wherein a hardness of the member is between 10 degrees and 40 degrees.

18. The equipment for preventing and treating pelvic organ prolapse as recited in claim 1, further comprising a supporting member for supporting the member.

19. The equipment for preventing and treating pelvic organ prolapse as recited in claim 18, wherein the supporting member is homogeneously integrated with the member or heterogeneously and adhesively integrated with the member.

20. The equipment for preventing and treating pelvic organ prolapse as recited in claim 18, wherein the supporting member is made of a material with hardness enough to maintain a form of the member.

21. The equipment for preventing and treating pelvic organ prolapse as recited in claim 20, wherein the hardness of the supporting member is between 40 degrees and 80 degrees.

* * * * *